(12) United States Patent
Qin (10) Patent No.: US 11,179,581 B2
(45) Date of Patent: Nov. 23, 2021

(54) SYSTEMS AND METHODS FOR PROMOTING CELLULAR ACTIVITIES FOR TISSUE MAINTENANCE, REPAIR, AND REGENERATION

(71) Applicant: The Research Foundation for The State University of New York, Albany, NY (US)

(72) Inventor: Yi-Xian Qin, Setauket, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 499 days.

(21) Appl. No.: 15/557,268

(22) PCT Filed: Mar. 8, 2016

(86) PCT No.: PCT/US2016/021317
§ 371 (c)(1),
(2) Date: Sep. 11, 2017

(87) PCT Pub. No.: WO2016/144931
PCT Pub. Date: Sep. 15, 2016

(65) Prior Publication Data
US 2018/0050223 A1    Feb. 22, 2018

Related U.S. Application Data

(60) Provisional application No. 62/130,513, filed on Mar. 9, 2015.

(51) Int. Cl.
*A61N 7/02* (2006.01)
*A61N 7/00* (2006.01)

(52) U.S. Cl.
CPC ........ *A61N 7/02* (2013.01); *A61N 2007/0095* (2013.01)

(58) Field of Classification Search
CPC .... A61N 7/00; A61N 7/02; A61N 2007/0004; A61N 2007/0034; A61B 8/44;
(Continued)

(56) References Cited

U.S. PATENT DOCUMENTS

| 4,337,661 A | 7/1982 | Kretz |
| 4,530,360 A | 7/1985 | Duarte |

(Continued)

FOREIGN PATENT DOCUMENTS

| CN | 1443084 | 9/2003 |
| CN | 102670264 | 9/2012 |

(Continued)

OTHER PUBLICATIONS

Bystritsky et al. 2015 Curr. Behav. Neurosci. Rep. 2:60-66; ePub Mar. 7, 2015 (Year: 2015).*

(Continued)

*Primary Examiner* — Michael J Tsai
*Assistant Examiner* — Patrick M Mehl
(74) *Attorney, Agent, or Firm* — The Farrell Law Firm, P.C.

(57) ABSTRACT

Stimulating cell activity within a tissue is performed by an ultrasound array transducer having a plurality of transducer elements and a controller that actuates a plurality of transducer elements to emit focused acoustic energy to a plurality of focal zone locations in a scan direction at a focal zone scan rate. The actuation of the plurality of transducer elements to emit focused acoustic energy to the plurality of focal zone locations in the scan direction at the focal zone scan rate is repeated for a plurality of sweep cycles at a sweep rate which stimulates cells for optimal tissue growth.

19 Claims, 11 Drawing Sheets

(58) Field of Classification Search
CPC ............... A61B 8/4477; A61B 8/4494; A61B 18/0206; A61B 18/00

See application file for complete search history.

(56) References Cited

U.S. PATENT DOCUMENTS

| | | | |
|---|---|---|---|
| 5,111,822 A | | 5/1992 | Dory |
| 6,508,774 B1 | | 1/2003 | Acker et al. |
| 6,645,162 B2 | | 11/2003 | Friedman et al. |
| 6,974,415 B2 | | 12/2005 | Cerwin et al. |
| 7,521,023 B2 | | 4/2009 | Laugharn, Jr. et al. |
| 7,687,026 B2 | | 3/2010 | Laugharn, Jr. et al. |
| 7,706,882 B2 | | 4/2010 | Francischelli et al. |
| 8,465,427 B1 * | | 6/2013 | Yi-Xian Qin ............ A61B 8/00 600/438 |
| 8,466,605 B2 | | 6/2013 | Kushculey et al. |
| 8,986,211 B2 | | 3/2015 | Gertner et al. |
| 9,011,336 B2 | | 4/2015 | Slayton et al. |
| 9,039,617 B2 | | 5/2015 | Slayton et al. |
| 11,058,900 B2 | | 7/2021 | Towe et al. |
| 2002/0082528 A1 | | 6/2002 | Friedman et al. |
| 2005/0124887 A1 * | | 6/2005 | Li ........................ A61B 8/4461 600/443 |
| 2006/0252045 A1 * | | 11/2006 | Chatterjee-Kishore ..................... C12Q 1/6876 435/6.13 |
| 2010/0076314 A1 | | 3/2010 | Muratore et al. |
| 2010/0204576 A1 | | 8/2010 | Adam |
| 2010/0241036 A1 | | 9/2010 | Vortman et al. |
| 2011/0077555 A1 | | 3/2011 | Wing et al. |
| 2012/0215099 A1 | | 8/2012 | Wallace |
| 2012/0289869 A1 * | | 11/2012 | Tyler ........................ A61N 7/00 601/2 |
| 2014/0316269 A1 * | | 10/2014 | Zhang .................. A61B 8/4494 600/439 |
| 2018/0263651 A1 | | 9/2018 | Hissong et al. |
| 2019/0030375 A1 | | 1/2019 | Zachar |
| 2019/0083817 A1 | | 3/2019 | Okusa et al. |
| 2020/0205782 A1 | | 7/2020 | Vortman et al. |
| 2020/0398084 A1 | | 12/2020 | Guha et al. |
| 2021/0170204 A1 | | 6/2021 | Vortman et al. |

FOREIGN PATENT DOCUMENTS

| | | | | |
|---|---|---|---|---|
| CN | 203253067 | 10/2013 | | |
| CN | 104936517 | 9/2015 | | |
| CN | 111801054 | 10/2020 | | |
| CN | 112888367 | 6/2021 | | |
| CN | 113260412 | 8/2021 | | |
| CN | 113286552 | 8/2021 | | |
| CN | 113329788 | 8/2021 | | |
| EP | 0 351 610 | 1/1990 | | |
| EP | 1 750 804 | 2/2007 | | |
| EP | 1 871 479 | 1/2008 | | |
| EP | 2 481 446 | 8/2012 | | |
| EP | 2 521 593 | 11/2012 | | |
| EP | 3 096 838 | 11/2016 | | |
| EP | 3 287 170 | 12/2018 | | |
| EP | 3 801 763 | 4/2021 | | |
| JP | 2004-511268 | 4/2004 | | |
| JP | 2009-508649 | 3/2009 | | |
| JP | 2013-106982 | 6/2013 | | |
| JP | 6067590 | 1/2017 | | |
| JP | 6470566 | 1/2019 | | |
| JP | 2019-51295 | 4/2019 | | |
| JP | 2019-529021 | 10/2019 | | |
| JP | 2020-505095 | 2/2020 | | |
| JP | 6819012 | 1/2021 | | |
| KR | 10-2007-0065332 | 6/2007 | | |
| KR | 10-1337250 | 12/2013 | | |
| KR | 10-2019-0041460 | 4/2019 | | |
| KR | 10-2021-0024672 | 3/2021 | | |
| WO | WO 01/70381 | 9/2001 | | |
| WO | WO 02/05897 | 1/2002 | | |
| WO | WO 2009/050719 | 4/2009 | | |
| WO | WO 2010/009141 | 1/2010 | | |
| WO | WO 2010/033867 | 3/2010 | | |
| WO | WO 2011/013001 | 2/2011 | | |
| WO | WO 2013/040443 | 3/2013 | | |
| WO | WO2013040443 A2 * | 3/2013 | ............... | A61N 5/00 |
| WO | WO 2013/048912 | 4/2013 | | |
| WO | WO 2014/001962 | 1/2014 | | |
| WO | WO 2014/137835 | 9/2014 | | |
| WO | WO 2014/164363 | 10/2014 | | |
| WO | WO 2015/074034 | 5/2015 | | |
| WO | WO 2016/144931 | 9/2016 | | |
| WO | WO 2019/186304 | 10/2019 | | |
| WO | WO 2019/186305 | 10/2019 | | |
| WO | WO 2020/131857 | 6/2020 | | |

OTHER PUBLICATIONS

Plaksin et al. 2014 Phys. Rev. X 4:011004 10 pages (Year: 2014).*
Mulgaonkar2014 PhD Thesis UCLA; 237 pages (Year: 2014).*
Vanderploeg et al. 2004 Journal of Biomechanics 37 (2004) 1941-1952 (Year: 2004).*
Desmoulin 2013 PhD Thesis Department of Mechanical and Manufacturing Engineering University of Calgary Canada 376 pages (Year: 2013).*
Chinese Office Action dated Nov. 27, 2018 issued in counterpart application No. 201680013055.3, 9 pages.
PCT/ISA/237 Written Opinion issued on PCT/US2016/019143, pp. 5.
Yi-Xian Qin et al., "Mechanotransduction in Musculoskeletal Tissue Regeneration: Effects of Fluid Flow, Loading, and Cellular-Molecular Pathways".
BioMed Research International, vol. 2014, Article ID 863421, Aug. 18, 2014, 12 pages.

* cited by examiner

SYSTEMS AND METHODS FOR PROMOTING CELLULAR ACTIVITIES FOR TISSUE MAINTENANCE, REPAIR, AND REGENERATION

CROSS-REFERENCE TO RELATED APPLICATIONS

This application claims the benefit of the filing date of U.S. Provisional Patent Application No. 62/130,513, filed Mar. 9, 2015, entitled "SYSTEM AND METHOD FOR PROMOTING CELLULAR ACTIVITIES FOR TISSUE REPAIR AND REGENERATION," which is incorporated by reference herein in its entirety.

GOVERNMENT RIGHTS

This invention was made with government support under AR061821 and AR052379 awarded by the National Institutes of Health. The government has certain rights in the invention.

TECHNICAL FIELD

The present invention relates generally to therapeutic ultrasound systems for treating human and animal tissue and more particularly, to therapeutic ultrasound systems that emit ultrasound signals capable of promoting cell activity for tissue growth.

BACKGROUND OF THE INVENTION

Musculoskeletal disorders represent a substantial burden for the health care system and significantly affect the quality of life for people who experience these disorders, particularly the aging population. Musculoskeletal disorders include deterioration to hard tissue (e.g. osteoporosis), deterioration to soft tissue (e.g. osteoarthritis); injuries to hard-tissue (e.g. fractures, non-union fractures, and stress fractures); and injuries to connective soft-tissue (e.g. torn or strained ligaments, tendons, and muscles). To minimize the impact of these musculoskeletal disorders, it is desirable to initiate and speed tissue growth, as well as mitigate tissue deterioration.

However, as we age tissue growth slows, making it unable to reduce deterioration and repair injury. This is because cells that form the tissue are less able to differentiate (specialize and mature to tissue cells), proliferate (growth and multiply), turn-over (replace old cells or change types), and regulate (maintain homeostasis). In addition, reduced physical activity causes reduced blood flow and interstitial fluid flow (fluid in the tissue that provides cells with nutrients and waste removal, as well as physical shear stress). Therefore, a major goal in optimizing tissue maintenance, repair, and regeneration is to increase cell differentiation, cell perforation, motility, cell regulation, tissue remodeling, tissue regeneration, mineralization, blood flow, and interstitial fluid flow in the region of interest.

It is well known that cells in the body respond to mechanical loading. Cellular mechanisms convert the mechanical loading into chemical activity (mechanotransduction), which increases cell differentiation and regulation. For years, acoustic energy in the form of low intensity pulsed ultrasound ("LIPUS") has been used to provide mechanical loading to tissue to accelerate healing (see U.S. Pat. No. 4,530,360 to Duarte).

However, studies investigating the results of ultrasound on accelerating healing have produced inconsistent results. One explanation for the inconsistency is the lack of a comprehensive understanding of the biological mechanisms at work in the complex process of tissue growth. Researchers have worked very hard over the past several decades in an attempt to understand the effect of physical stimuli on tissue growth. Recent findings have given a better understanding of the biological mechanisms at work. It has been found that in addition to cell proliferation and differentiation; calcium release, gene expression, cellular and molecular pathway signaling, and nutrient transportation are important components of tissue growth. In a new study, it has been discovered that mechanical loading and fluid flow induces these biological mechanisms. See Qin, Yi-Xian and Hu, Minyi "Mechanotransduction in Musculoskeletal Tissue Regeneration: Effects of Fluid Flow, Loading, and Cellular-Molecular Pathways," *Hindawi Publishing Corp. BioMed Research International*, Epub 2014 Aug. 18, PMID: 25215295, which is herein incorporated by reference.

Prior art ultrasound systems emit acoustic pressure waves for providing loading to the tissue and the cells, however the acoustic pressure waves emitted by those systems do not induce controlled fluid flow within the tissue. Therefore, there is a need to provide an ultrasound system that emits acoustic energy to provide mechanical loading and induce controlled fluid flow within the tissue for enhanced and consistent tissue maintenance, repair, and regeneration.

SUMMARY OF THE INVENTION

It is accordingly an object of the present invention to provide ultrasound systems and methods for emitting acoustic energy in a manner that provides mechanical loading and induce controlled fluid flow for enhanced and consistent tissue maintenance, repair, and regeneration. The invention in its presently preferred form achieves the foregoing objectives by emitting focused acoustic energy to locations within a region of interest ("ROI") at a scan rate in a scan direction to induce fluid flow within the tissue. The cycle of emitting focused acoustic pressure waves and inducing fluid flow is repeated at a sweep rate that consistently stimulates cell activity in the ROI. Unlike prior art systems where the fluid flow may have been generated unexpectedly and randomly, the fluid flow created by the ultrasound systems and methods of the present invention is controlled and consistent. The ultrasound systems and methods of the present invention induce a pressure gradient, a sheer stress, interstitial fluid flow, a strain rate, a strain gradient, and a loading at a frequency necessary for calcium release, gene expression, cellular and molecular pathway signaling activation, and nutrient transportation; thus providing enhanced and consistent cellular stimulation for tissue maintenance, repair and regeneration.

The present invention comprises methods, systems, and a controller for achieving the foregoing objectives. The systems comprise an ultrasound array transducer having a plurality of transducer elements and a controller. In different embodiments, the ultrasound array transducer may have a linear format, including a linear array and a phased array; or a two-dimensional format, including a two-dimensional matrix and an annular ring. The controller is programmed to actuate the transducer to emit focused acoustic energy as described below.

The methods of the present invention comprise locating the ultrasound array transducer having a plurality of transducer elements in the vicinity of the ROI, and actuating the plurality of transducer elements to emit focused acoustic energy to a plurality of focal zone locations in a scan direction at a focal zone scan rate. The actuating of the plurality of transducer elements to emit focused acoustic energy to the plurality of focal zone locations is repeated for a plurality of sweep cycles at a sweep rate.

In various embodiments, the scan direction is opposite for alternate sweep cycles. In some embodiments, the focal zone locations are uniformly spaced throughout the region of interest. In some embodiments, actuating the plurality of transducer elements to emit focused acoustic energy to the plurality of focal zone locations is performed in two spatial dimensions or in three spatial dimensions.

In various embodiments, the focused acoustic energy may have an intensity in the range of 5 mW/cm$^2$ to 180 mW/cm$^2$ at the region of interest to provide a therapeutic treatment. In the various embodiments, the focal zone scan rate may be in the range of 0.2 kHz to 0.5 MHz and the sweep rate may be in the range of 0.2 Hz to 1 kHz.

In various embodiments, performing the plurality of sweep cycles may occur for a treatment duration that may have a time range of five minutes to sixty minutes. In some embodiments, the treatment duration may include a rest period. The therapeutic treatment may be repeated over periods of days to promote tissue growth.

DETAILED DESCRIPTION

Figure 1:
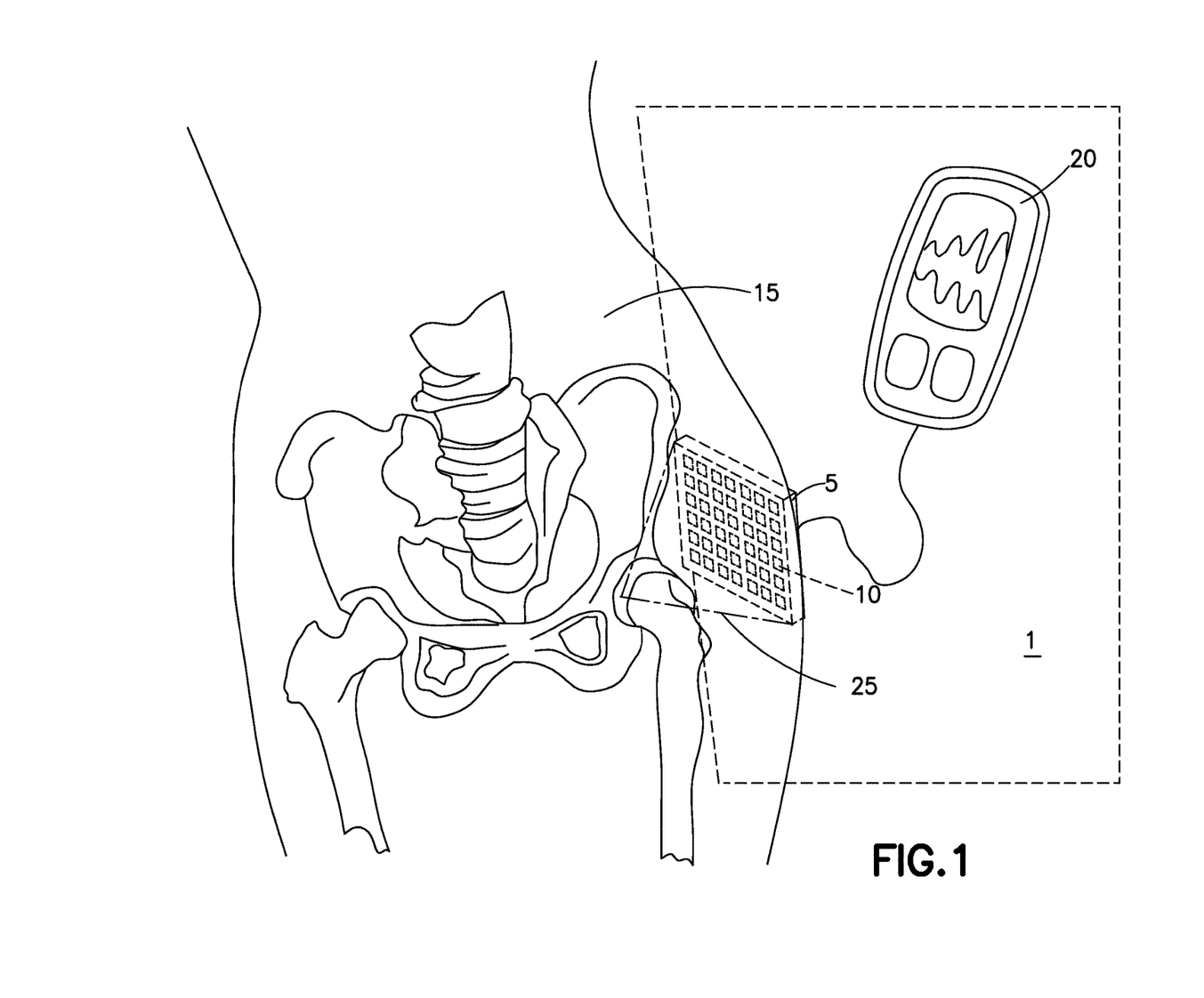
FIG. 1 shows an illustration of an example ultrasound system emitting focused acoustic energy to a region of interest.

The invention will be described in detail for a presently preferred embodiment, in conjunction with the accompanying drawings. Referring to FIG. 1, an example of an ultrasound system 1 emitting focused acoustic energy 25 to a region of interest ("ROI") is shown. The ultrasound system 1 of the present invention has an ultrasound array transducer 5 having a plurality of transducer elements 10 and a controller 20 programmed to actuate the plurality of transducer elements 10 to emit focused acoustic energy 25 in a manner that provides mechanical loading and induces controlled fluid flow for enhanced and consistent tissue maintenance, repair, and regeneration. The ultrasound array transducer 5 may communicate with the controller 20 over a wired connection or a wireless connection. The ultrasound array transducer 5 may be held in place for the treatment by hand or may be part of a wearable device that holds it in place for the treatment duration. The ultrasound array transducer 5 can be coupled to the skin surface of a body 15 or directly to tissue surfaces, such as bone or cartilage tissue, as known to one skilled in the art.

By way of illustration, FIG. 1 shows the focused acoustic energy 25 targeting the femoral neck within a patient's body 15. It should be understood that the ROI may be within any tissue (soft or hard), external or internal to a body 15 (human or animal), and includes any region (e.g. arms, hands, legs, feet, hips, shoulders, knees) within the body 15 in which cell stimulation is being promoted. Cell stimulation may be used for fracture healing, bone regeneration, bone repair, bone density maintenance, bone grafting, skeletal reconstruction of bone defects, stem cell differentiation to the different pathways, tissue engineering, enhancing drug delivery, gene therapy, and chondrocyte differentiation in the formation of cartilage, ligaments and tendons.

The phrase "in a vicinity of the region of interest" as used herein means an area near the tissue receiving targeted focused acoustic energy. For example, as shown in FIG. 1, the ultrasound array transducer 5 is physically positioned on the patient's body 15 in the hip area in order to focus the acoustic energy 25 to the femoral neck. Placement of the ultrasound array transducer 5 on the hip also allows treatment of the great trochanter region and cartilage in the joint of the hip. Similarly, placement of the ultrasound array transducer 5 on the leg allows treatment of a tibia bone fracture, placement of the ultrasound array transducer 5 on the knee allows treatment of cartilage in the knee joint, and placement of the ultrasound array transducer 5 on the shoulder allows treatment of cartilage in the shoulder.

Figure 2:
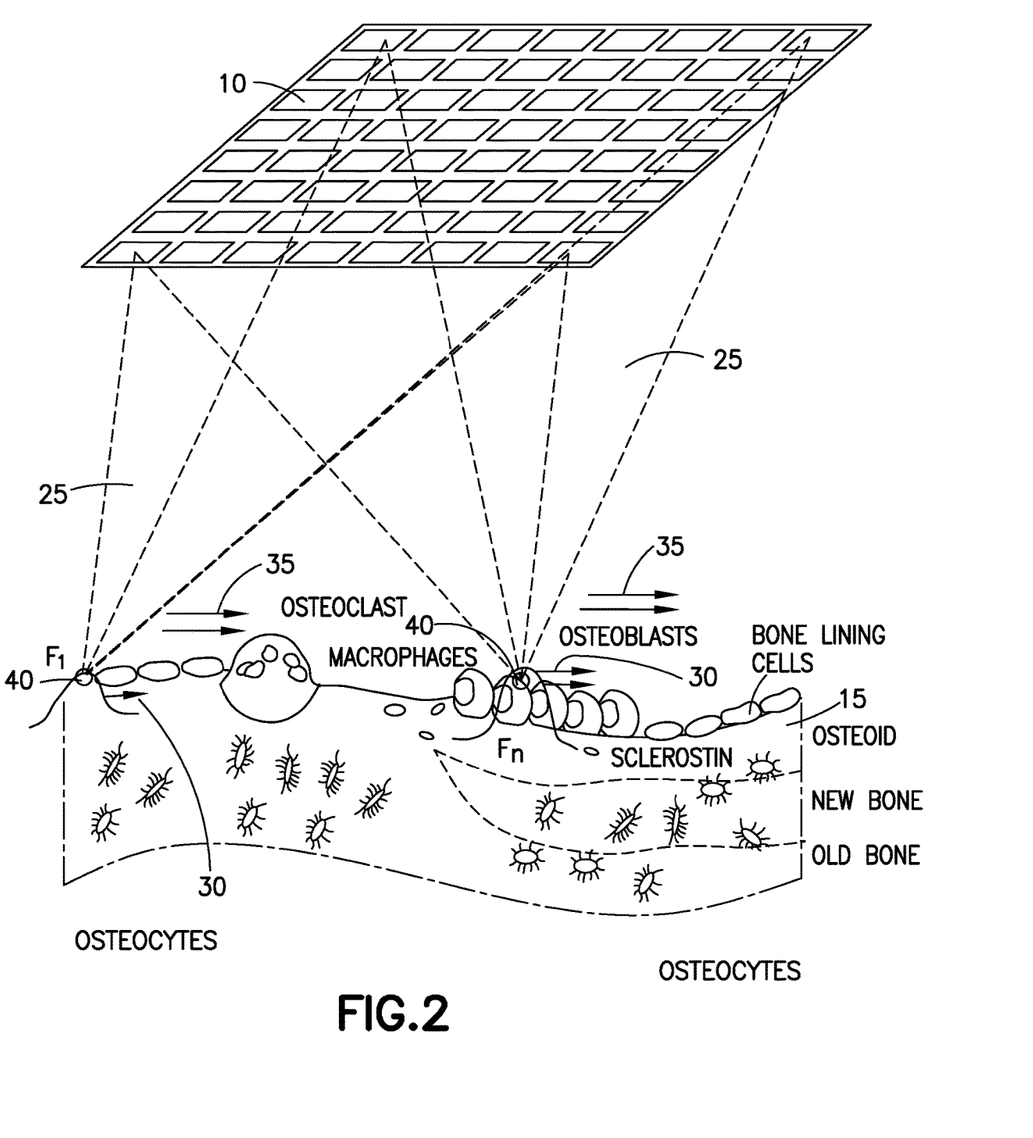
FIG. 2 shows a high level illustration of an example ultrasound array transducer emitting focused acoustic energy to stimulate molecular and cellular mechanisms.

Referring to FIG. 2, an illustration of a plurality of transducer elements 10 emitting focused acoustic energy 25 to stimulate tissue response through molecular and cellular mechanism activation is conceptually illustrated. The plurality of transducer elements 10 are actuated to emit acoustic energy that combines to form a focal zone 40 at a focal zone location, shown as F1. The term "focal zone" as used herein means the resulting point, area, line, or volume at the targeted location of the focused acoustic energy 25. The term "focal zone location" means the location within the tissue in which a focal zone 40 impinges on the tissue cells. The first of the plurality of focal zone locations is shown as F1 and the last of the plurality of focal zone locations is shown as Fn in this illustration. Each focal zone 40 creates a pressure gradient 30 in the nearby tissue, which provides a local shear stress to the cells.

At a time interval after emitting acoustic energy 25 to focal zone location F1, the plurality of transducer elements 10 are then actuated to emit acoustic energy 25 that combines to form an additional focal zone 40 (not shown), which is displaced from the first focal zone location F1. The focal zone locations may be uniformly spaced throughout the treatment region or may be selected as a biased pattern, where some focal zone locations are located closer together while others are more spatially separated. The actuation of the plurality of transducer elements 10 to form the focal zones 40 is repeated for n focal zone locations, shown as Fn. The term "focal zone scan rate" as used herein means the rate of generating the focal zones 40 at the different focal zone locations, F1 to Fn. The term "scan direction" as used herein means the direction of movement of the focal zone 40 from one focal zone location to the next focal zone location, i.e. from F1 towards Fn.

The impingement of the focal zone 40 on the cells in the tissue generates a pressure wave which induces a pressure gradient 30. When another pressure wave is generated within a certain time and distance, the pressure gradient 30 is enhanced because the cells of the tissue do not recover to their original position. The enhanced pressure gradient 30 induces fluid flow 35 in the same direction as the scan direction. The term "sweep cycle" as used herein means the sequence for emitting focused acoustic energy 25 in a scan direction to a plurality of focal zone locations that encompass a ROI. The ROI is used loosely to include the treatment area (region) or a portion of the treatment area.

In the present invention, the sweep cycle is performed for a plurality of times; i.e. F1 to Fn, F1 to Fn, F1 to Fn . . . . In some embodiments, the scan direction is opposite for alternate sweep cycles, i.e. from F1 to Fn in one sweep cycle; and then from Fn to F1 in the next sweep cycle. The term "sweep rate" as used herein means repetition rate of performing the sweep cycle. Sweep cycles may be performed for the duration of the treatment time. The term "treatment" as used herein means the use of therapeutic ultrasound (or acoustic) energy to affect cells within tissue. The term "treatment duration" as used herein means the duration of time that the treatment is used to affect cells within tissue, which may be in the range of five to sixty minutes per day, preferably in the range of fifteen to twenty minutes per day.

The various embodiments of the present invention may have different ultrasound array transducer configurations, focal zone sizes, focal zone scan rates, focal zone locations, scan directions, sweep rates, acoustic energy levels, and acoustic frequency; as described below. However, unlike the prior art systems where the fluid flow 35 may have been generated unexpectedly and randomly, the different embodiments of the present invention create controlled and enhanced fluid flow 35. In addition, unlike the prior art systems where acoustic pressure from the acoustic energy is dilational and compresses cells in the ROI, the various embodiments of the present invention emit pressure waves that induce pressure gradients 30 with a deviatoric effect on the cells. The deviatoric effect, which presses the cells to the side rather than compressing them, occurs in the scan direction because as the focused acoustic energy 25 is transmitted to each focal zone location at the focal zone scan rate, the pressure gradient 30 is enhanced in the scan direction. This deviatoric effect has been shown to stimulate the cells' membrane.

In some embodiments, the pressure gradient 30 and fluid flow 35 may be induced in two or three spatial dimensions, as described below. Two (or three) dimensional pressure gradients 30 and fluid flow 35 may stimulate different cell types at different local anatomic locations. The two (or three) dimensional pressure gradients 30 and fluid flow 25 may also stimulate cellular response through various spatial channels within the tissue. This may compensate for tissue that is anisotropic and in-homogenous.

In the various embodiments of the present invention, the ultrasound array transducer 5 may have different configurations. In the preferred embodiment, the ultrasound array transducer 5 is a non-invasive ultrasound transducer. The ultrasound array transducer 5 may be a linear array, a phased array, a two-dimensional matrix, or an annular ring. The linear array and the phased array may contain any number of transducer elements 10. The two-dimensional matrix may be any size with any number of transducer elements 10, including for example 2×2, 2×6, 5×5, 10×5, 25×25, etc. The annular ring may contain any number of ring sections as transducer elements 10. The controller 20 may actuate all the transducer elements 10 to form the focal zone 40 or may actuate a portion of the transducer elements 10 to form the focal zone 40. Different aspects of the present invention may be described herein in terms of various configurations of the ultrasound array transducer 5. However, it should be appreciated that the different aspects of the present invention may be realized with many ultrasound array transducer 5 configurations and controller 20 configurations.

Figure 3A:
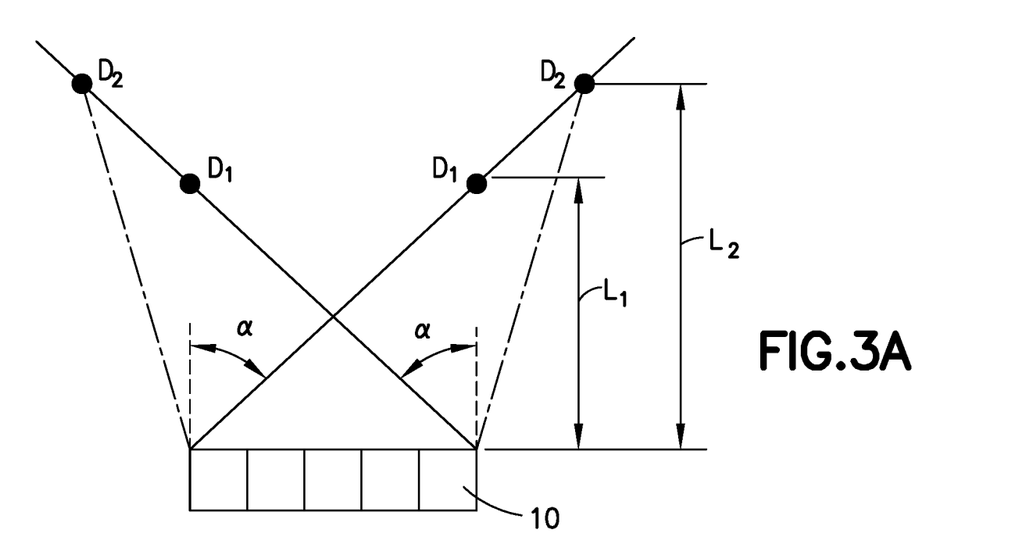
FIG. 3A shows a drawing of an example linear array transducer and its maximum sweep distance.

Referring to FIG. 3A, an example linear array or phased array transducer 5 with five transducer elements 10 is shown. The size of the linear array or phased array transducer 5 may be dependent on the number of transducer elements 10, the size of the transducer elements 10, the pitch size, and the packaging of the ultrasound array transducer 5. The length of the ultrasound array transducer 5 provides a steering angle α, as known to one skilled in the art. The steering angle α and the distance from the ultrasound array transducer 5 to the ROI, shown as $L_1$ and $L_2$, form the maximum distance that can be covered in a sweep cycle, shown as $D_1$ and $D_2$ respectively. However, the distance covered by a sweep cycle may be selected to match the ROI, which is typically a smaller distance than the maximum distance that can be covered in a sweep cycle. When treating tissue injury or deterioration within the body 15, the ROI corresponds to the size of a bone defect or damaged cartilage, which is typically in the range of 1 cm to 3 cm. It should be understood that the ROI may be larger for other types of treatments, i.e. bone maintenance.

To determine the focal zone locations throughout the ROI, the size of the focal zone 40 may be selected first. Preferably the focal zone size is selected to match the cell size in the tissue to be stimulated. This may be in the range of 1 μm to 100 μm depending on tissue type. However, the focal zone size can be expanded to 1 mm and still generate a sufficient pressure gradient 30 and fluid flow 35 within the ROI. The number of focal zones 40 may be determined by dividing the size of the ROI by the size of the focal zone 40 to allow the focal zones 40 to be evenly located over the ROI. However, it should be understood that other focal zone location patterns may be used, such as a bias pattern.

Figure 3B:
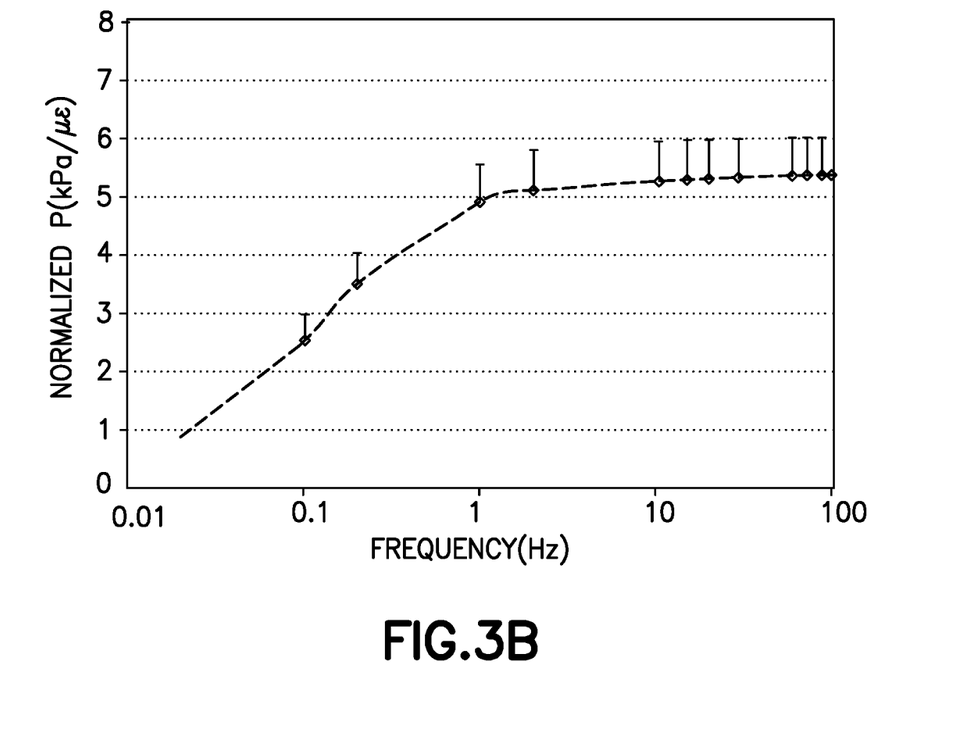
FIG. 3B shows a graph that illustrates the loading response.

The focal zone scan rate is preferably selected to enhance the pressure gradient 30, and is dependent on the cell response rate, which is in the range of 2.0 Hz to 1 MHz, depending on the cell type. Therefore, the focal zone scan rate is preferably selected to be in the range of 0.2 kHz to 0.5 MHz, and more preferable in the range of 10 kHz to 500 kHz. The focal zone scan rate, focal zone size, and size of the ROI may be selected in combination to meet the sweep rate requirements for tissue growth, as shown in FIG. 3B. The graph of FIG. 3B shows that as the loading rate is increased, the loading induced pressure in the tissue increases. The loading induced pressure induces the pressure gradient 30, which increases fluid flow 35 and initiates tissue adaption and growth. FIG. 3B shows that at lower loading rates, 0.1 Hz-1 Hz, the loading induced pressure in the tissue is increased three-fold. At loading rates of approximately 20 Hz, the loading induced pressure in the tissue starts to plateau and at loading rates of approximately 60 Hz, the loading induced pressure in the tissue reaches a threshold. Hence, optimal tissue growth may be achieved at a loading rate between 0.1 Hz and 500 Hz (above this rate the cells may be over stimulated). Since the sweep rate is twice the loading rate; for optimal tissue growth, the sweep rate may be in the range of 0.2 Hz to 1 kHz, and more preferably in the range of 2 Hz to 240 Hz. The focal zone scan rate, focal zone size, and size of the ROI are preferably selected in combination to accomplish a sweep rate for optimal tissue growth.

Thus, if the ROI is selected, for example as 1cm, which is typical for fracture healing and bone repair, and the focal zone size is selected to be 10 μm, then the number of focal zones becomes 1 cm/10 μm=1000. The focal zone scan rate can then be selected as 100 kHz, to provide a sweep rate of 100 Hz (the sweep rate equals the focal zone scan rate divided by the number of focal zones, in this embodiment).

Table 1 provides additional examples of corresponding ROI sizes, focal zone sizes, focal zone scan rates, and sweep rates for this example embodiment. It should be understood that these parameters may vary in the various embodiments of the present invention.

TABLE 1

| ROI | Focal Zone Size | Number of Focal Zones | Focal Zone Scan Rate | Sweep Rate |
| --- | --- | --- | --- | --- |
| 2 cm | 10 μm | 2000 | 200 kHz | 100 Hz |
| 3 cm | 10 μm | 300 | 10 kHz | 33 Hz |
| 4 cm | 50 μm | 800 | 16 kHz | 20 Hz |
| 5 cm | 50 μm | 1000 | 100 kHz | 100 Hz |

Figure 4A:
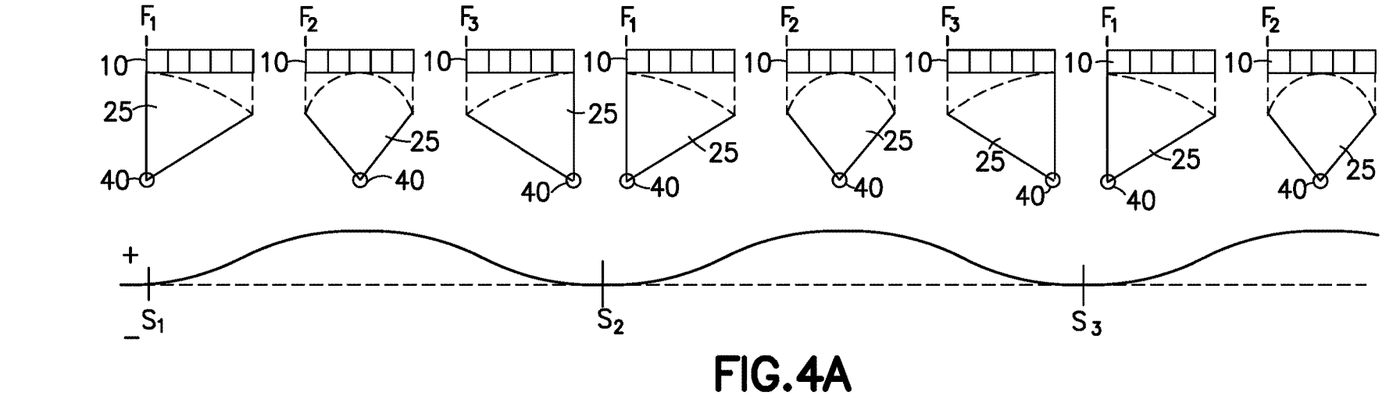
FIG. 4A shows a drawing of an example linear array transducer and a corresponding graph of an oscillatory acoustic energy pattern generated by multiple sweep cycles.

Referring to FIG. 4A, an example linear array or phased array transducer 5 with five transducer elements 10 is shown emitting focused acoustic energy 25 to a plurality of focal zone locations. For simplicity, only three focal zones 40 are shown, with focal zone locations of left, center, and right. However, it should be understood that there may be many other focal zones 40 located between the left and right focal zone locations. The scan direction for each sweep cycle may provide an oscillatory pattern, which is shown in the corresponding graph below the linear arrays. This graph shows the acoustic energy at the center of the ROI for a consistent scan direction. It can be seen that the acoustic energy increases and decreases as the focal zone 40 moves across the center of the ROI in the scan direction, shown as the "+" direction. The cells in this oscillatory pattern are pushed in the scan direction (and then recover to their resting position) at the sweep rate.

Figure 4B:
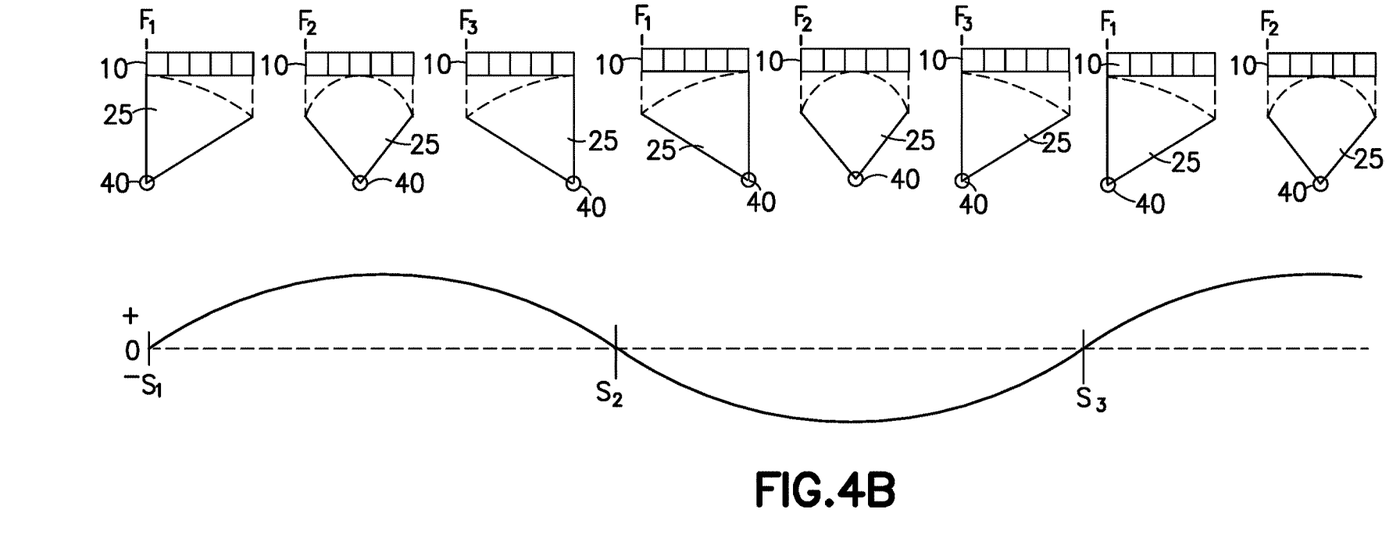
FIG. 4B shows a drawing of an example linear array transducer and a corresponding graph of a sinusoidal acoustic energy pattern generated by multiple sweep cycles.

Referring to FIG. 4B, an example linear array or phased array transducer 5 with five transducer elements 10 is shown emitting focused acoustic energy 25 to a plurality of focal zone locations. In this example, the scan direction is from left to right in one sweep cycle and then from right to left in the next sweep cycle. The opposing scan directions provides a sinusoidal pattern, which is shown in the corresponding graph below the linear arrays. This graph shows the acoustic energy pattern at the center of the ROI. It can be seen that the acoustic energy 25 increases and decreases as the focal zone 40 moves across the center of the ROI from left to right in the first sweep cycle, shown as the "+" direction; and then the acoustic energy 25 increases and decreases in the opposite direction in the second sweep cycle, shown as the "−" direction. The cells in this sinusoidal pattern are pushed in one direction and recover to their resting position in the first sweep cycle; and in the next sweep cycle, the cells are pushed in the opposite direction and recover to their resting position.

Figure 5A:
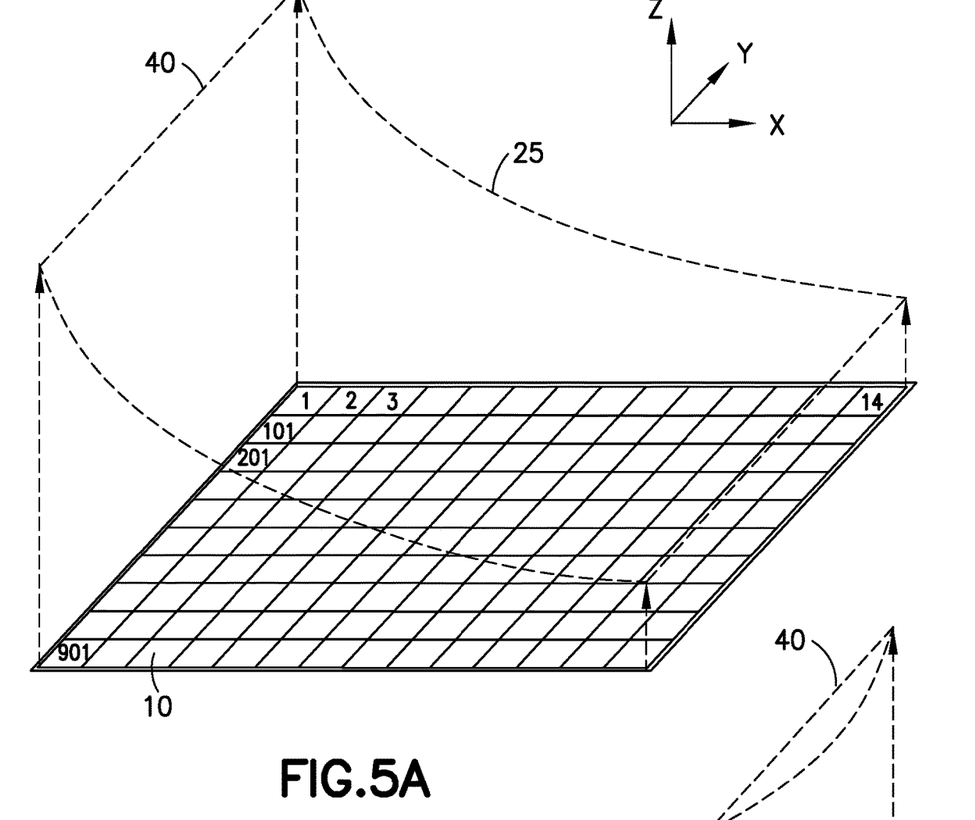
FIG. 5A shows a drawing of an example two-dimensional matrix and an example acoustic energy focal zone emitted from the two-dimensional matrix.
Figure 5B:
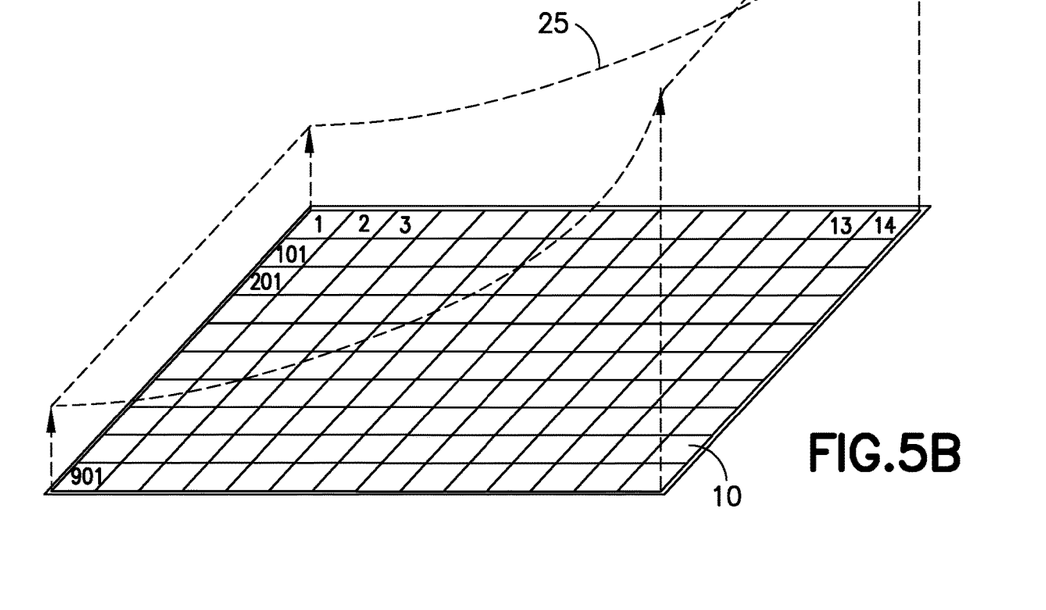
FIG. 5B shows a drawing of an example two-dimensional matrix and an example acoustic energy focal zone emitted from the two-dimensional matrix.
Figure 5C:
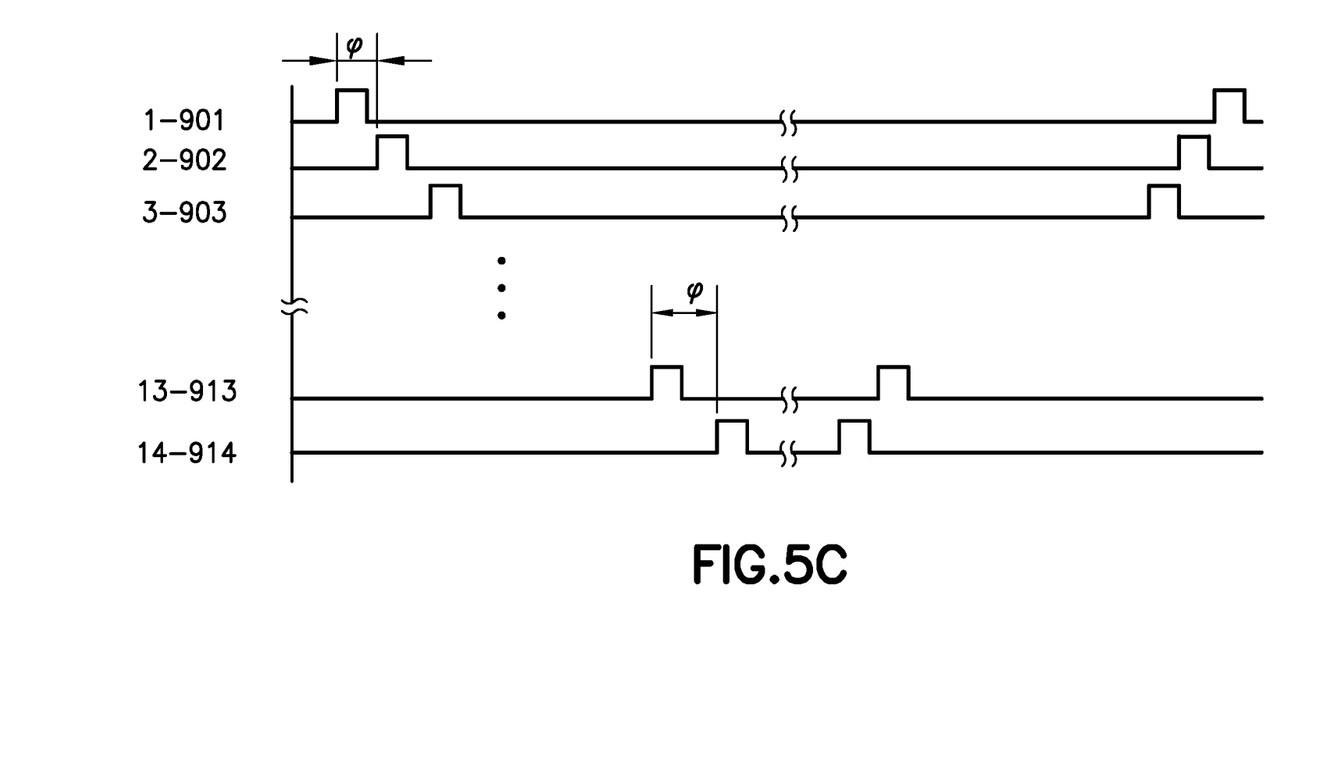
FIG. 5C shows a graph that illustrates the actuation sequence of the plurality of transducer elements to generate the example acoustic energy focal zones shown in FIGS. 5A and 5B.

Referring to FIG. 5A, an example two-dimensional matrix with a plurality of transducer elements 10 emitting focused acoustic energy 25 as a line focal zone 40, is shown at the beginning of a sweep cycle (focusing to the left). Referring to FIG. 5B, the same two-dimensional matrix with the plurality of transducer elements 10 emitting focused acoustic energy 25 as a line focal zone 40, is shown at the end of the sweep cycle (focusing to the right). Referring to FIG. 5C, the graph shows the actuation sequence for emitting focused acoustic energy 25 in line focal zones 40, as shown in FIGS. 5A and 5B. In this embodiment, determining the focal zone locations, as described above, may be accomplished using the size of the width of the line focal zone 40. In this example, the length of the line focal zone 40 allows a two-dimensional cell stimulation. In this example, the scan direction is across the x axis with stimulation to cells along the y-axis. However, in other embodiments, the scan direction may along the y-axis or a diagonal axis of the two dimensional matrix.

In some embodiments, the cell stimulation may take place along two axes including along the z-axis (perpendicular to the x-y axis) for a three-dimensional cell stimulation. For cell stimulation along the z-axis, the depth of the acoustic energy 25 varies. This may be accomplished by increasing (and/or decreasing) the power of the acoustic energy 25 at the focal zone scan rate in the scan direction. This also may be accomplished by focusing the focal zone 40 proximal to distal (or distal to proximal) at the focal zone scan rate in the scan direction. When cell stimulation takes place along two or three axes, emitting the focused acoustic energy 25 along one axis may be interleaved emitting the focused acoustic energy 25 along another axis (or two other axes) during each sweep cycle.

Figure 6A:
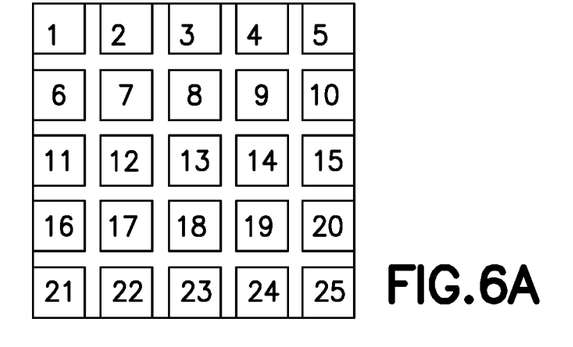
FIG. 6A shows a drawing of an example two-dimensional matrix with numbered transducer elements.
Figure 6B:
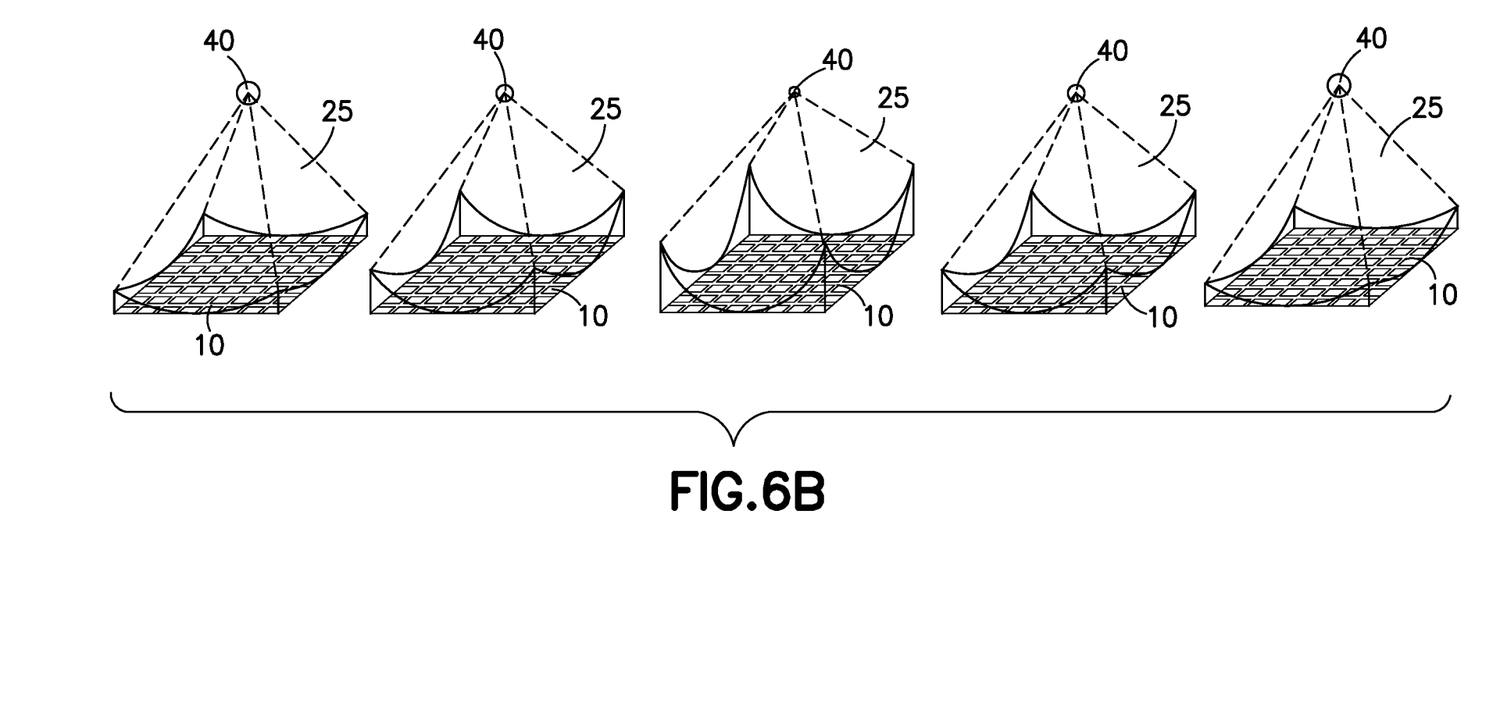
FIG. 6B shows a drawing of the two-dimensional matrix of FIG. 6A providing focused acoustic energy for different focal zone volumes.
Figure 6C:
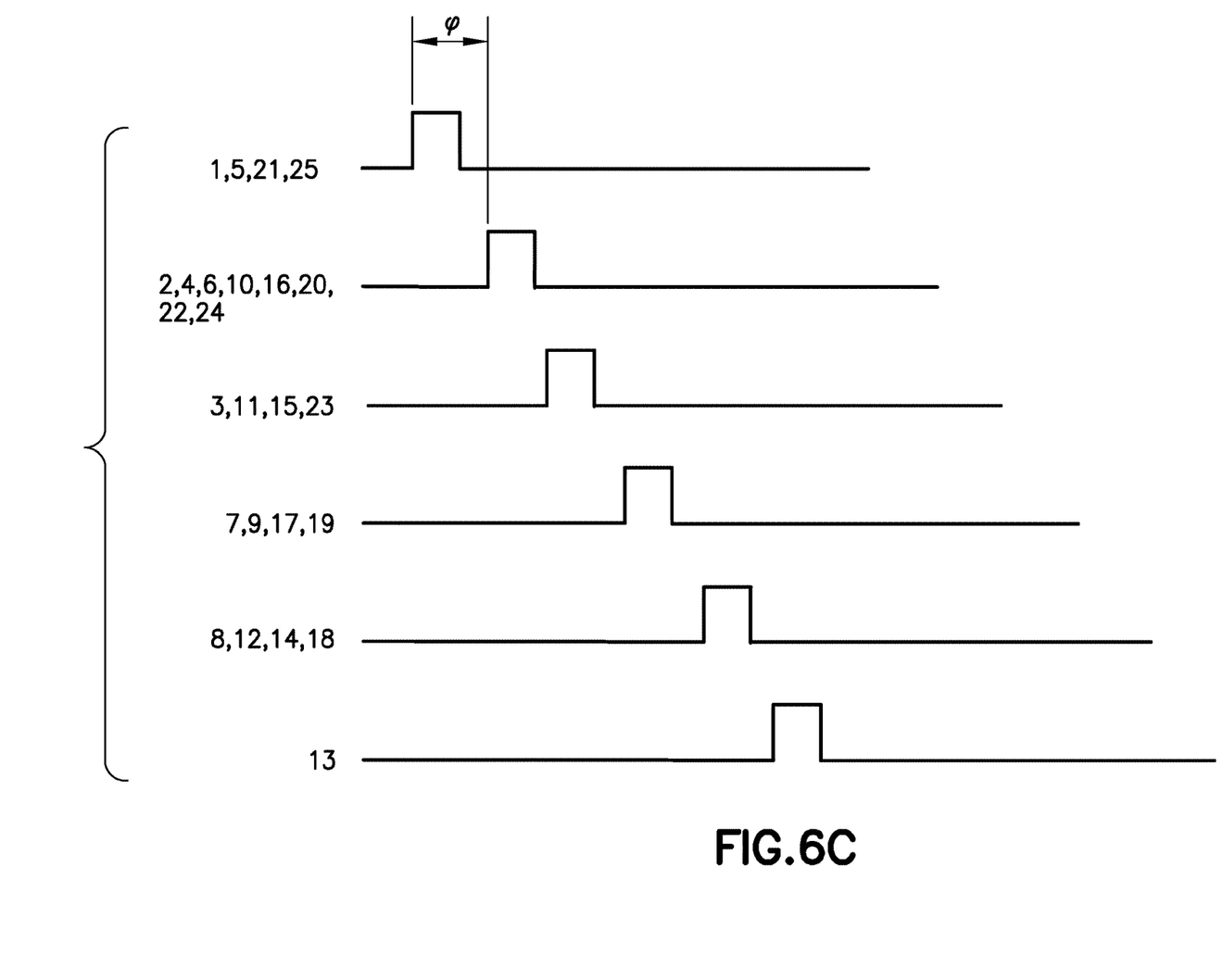
FIG. 6C shows a graph that illustrates the actuation sequence of the numbered transducer elements to generate the focal zones shown in FIG. 6B.

Referring to FIG. 6A, an example two-dimensional matrix with a numbered plurality of transducer elements 10 is shown. Referring to FIG. 6B, the two-dimensional matrix of FIG. 6A is shown emitting a volume of focused acoustic energy 25 for a three-dimensional cell stimulation. Referring to FIG. 6C, the timing of the actuation sequence of the plurality of transducer elements 10 is shown for creating the volume of focused acoustic energy 25 shown in FIG. 6B. In this embodiment the center of the focal zone 40 remains stationary and the size of the focal zone 40 is varied to create a volumetric pressure gradient 30. In this embodiment, the different sizes of the focal zone 40 correspond to the different focal zone locations in the embodiments described above, and may be similarly selected. The size of the focal zone 40 is increased (or decreased) at the focal zone scan rate. In this example, the focus size of the focal zone 40 starts at a larger size, becomes smaller, and then becomes larger creating a sinusoidal pattern.

Figure 7:
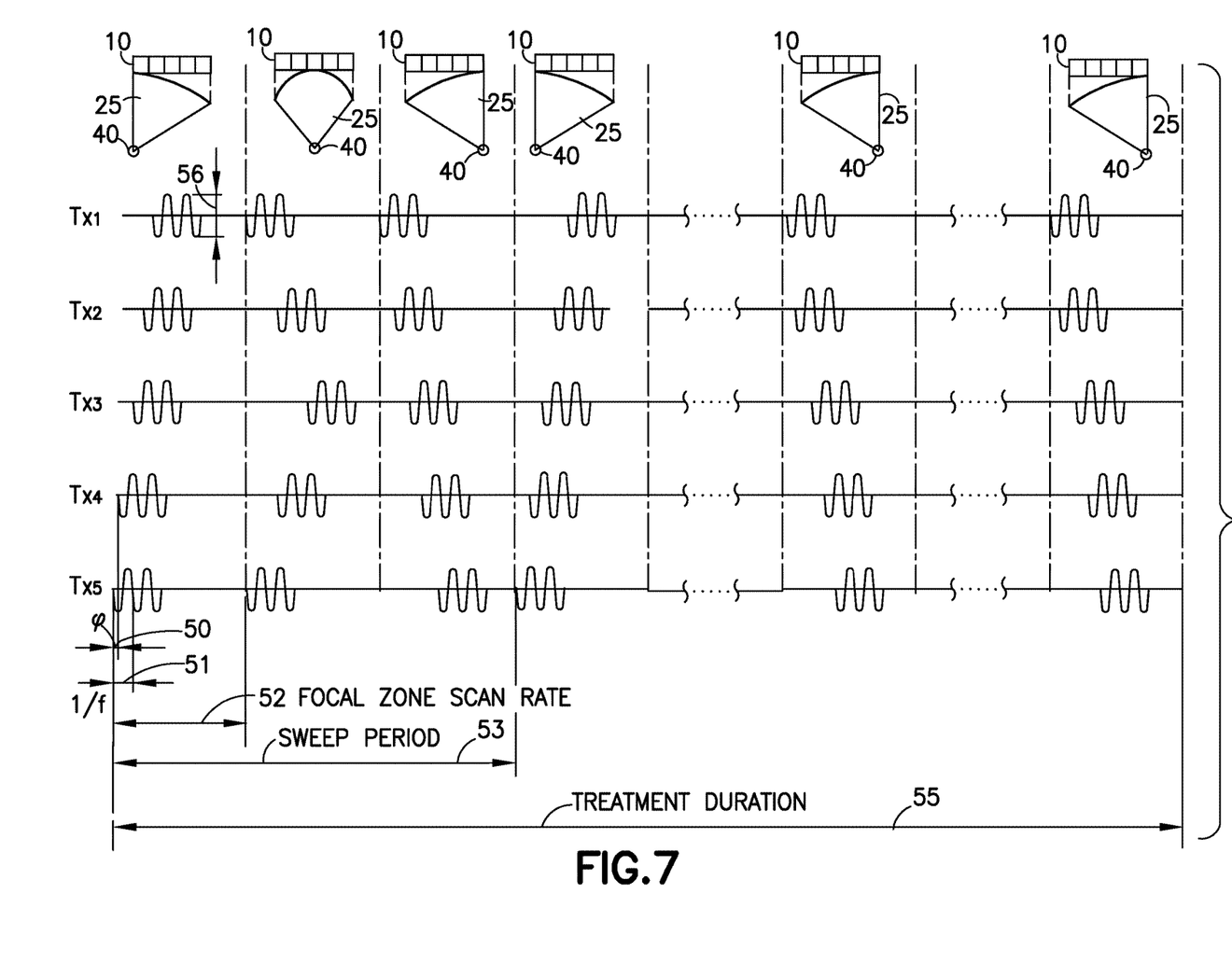
FIG. 7 shows a graph that illustrates the acoustic energy parameters and timing for a plurality of transducer elements for one embodiment of the present invention.

Referring to FIG. 7, an example linear array or phased array transducer 5 with five transducer elements 10 is shown emitting focused acoustic energy 25 to a plurality of focal zone locations. For simplicity, only three focal zones 40 are shown, in focal zone locations of left, center, and right; however, as above, it should be understood that there may be many other focal zones 40 located between the left and right focal zone locations. Beneath each depicted focal zone 40, is a graph showing the corresponding acoustic signals from each of the five transducer elements 10, shown as $Tx_1$, $Tx_2$, $Tx_3$, $Tx_4$, and $Tx_5$. Below the graph is a chart indicating the timing parameters of the acoustic signals that contribute to cell stimulation for tissue maintenance, repair, and regeneration. It should be understood that the timing parameters will be different for the various embodiments and configurations of the ultrasound system 1.

The phase difference 50 between the emitted acoustic signals, $Tx_1$, $Tx_2$, $Tx_3$, $Tx_4$, and $Tx_5$, creates the focused acoustic energy 25, as known to one skilled in the art. The phase differences 50 between the emitted acoustic signals, $Tx_1$, $Tx_2$, $Tx_3$, $Tx_4$, and $Tx_5$, may vary as a function of the focal zone location, the size of the focal zone, and the frequency of the acoustic signals.

The frequency 51 of the acoustic signals is depicted in this chart as a time period (1/f). The frequency 51 may be selected based on the tissue type being treated. In the preferred embodiments, the frequency of the ultrasound signals for hard tissue treatment is in the range of 0.3 MHz to 3.5 MHz, more preferably between 0.5 MHz to 1.5 MHz. In the preferred embodiments, the frequency of the ultrasound signals for soft tissue treatment is in the range of 0.5 MHz to 7.5 MHz, more preferably between 1.0 MHz to 2.5 MHz.

The focal zone scan period 52 is one over the focal zone scan rate. The focal zone scan rate is selected as described above. The term "duty cycle," as used here in, means the time the emission time of the acoustic signals, $Tx_1$, $Tx_2$, $Tx_3$, $Tx_4$, and $Tx_5$; in proportion the focal zone scan period 52. The duty cycle may be selected to be less than 100 percent to allow the cells to recover to a neutral status in order to respond to the next acoustic energy 25 emission. Because tissue may fatigue at a 100 percent duty cycle, in the preferred embodiments, the duty cycle of the acoustic signal emission is in the range of 10 percent to 80 percent.

The sweep period 53 is one over the sweep rate. The sweep rate is selected as described above. In the preferred embodiments, the power of the ultrasound beams 25 at the ROI is preferably low intensity ultrasound, in the range of 5 mW/cm$^2$ to 180 mW/cm$^2$, and more preferably between 20 mW/cm$^2$ to 80 mW/cm$^2$. These intensity levels are at the site of the ROI, not the actual output of the transducer elements 10. Since the acoustic signals, $Tx_1$, $Tx_2$, $Tx_3$, $Tx_4$, and $Tx_5$; from the actuated transducer elements 10 combine to produce the power of the focused acoustic energy 25 at the ROI, the intensity 56 of the ultrasound signal is dependent on the ultrasound array transducer 5 configuration and the location of the ROI.

In some embodiments, the power of the focused acoustic energy 25 at the focal zone 40 may have a programmed profile in which the focused acoustic energy 25 power may be controlled as a function the focus zone location, in which the power of the focused acoustic energy 25 emitted to one focal zone 40 may be greater than the power of the focused acoustic energy 25 emitted to a neighboring focal zone location. This may create a spatial acoustic energy gradient, which may generate a customized pressure gradient 30. In addition, the power of the focused acoustic energy 25 emitted to each focal zone 40 may have an energy profile that is different for each focal zone location. The energy profile may be repeated for each sweep cycle.

The treatment duration 55 may last a number of minutes; for example, for bone healing, fifteen to twenty minutes per day. Furthermore, the ultrasound system 1 may be used for a number of days per week for a number of weeks; for example, for bone healing approximately four to six weeks. Different types of tissues may require a different treatment duration, which may take place over a different number of days per week, and/or a different number of weeks. In some embodiments, the treatment duration 55 may include a rest period, which may be in a pattern, for example: repeating a five-minutes-on/five-minutes-off pattern or applying the treatment five minutes in the morning, afternoon, and evening. Different types of tissues may require applying the treatment on alternative days of the week such as Monday, Wednesday, and Friday. Furthermore, after performing the treatment for a number of days, which may be in the range of 20 to 150 days, preferably 30 to 90 days, a rest period of a number of days, such as 30 days, may be taken before repeating the treatment.

Figure 8:
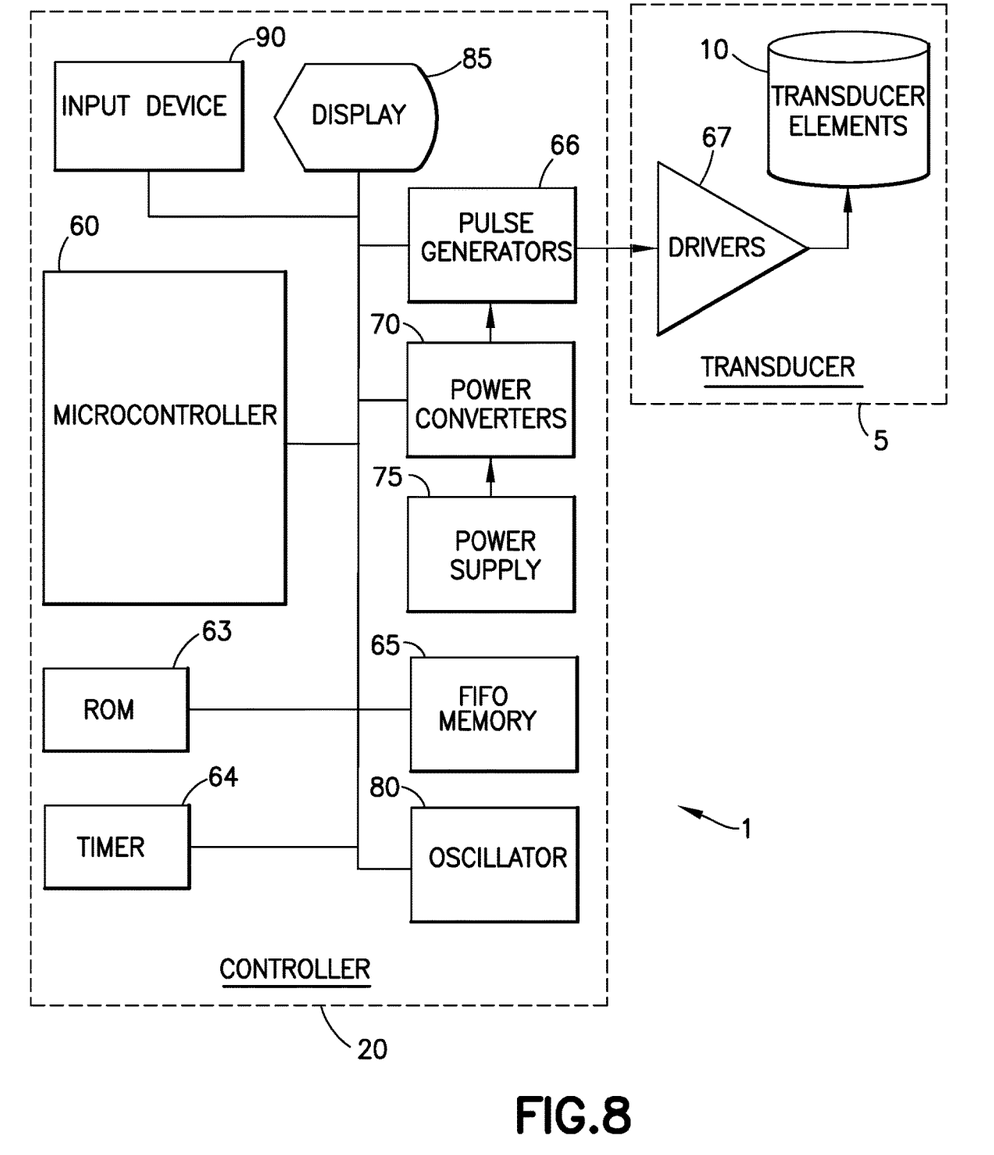
FIG. 8 shows a block diagram that illustrates an embodiment of a system of the present invention.

Referring to FIG. 8, a block diagram of the preferred embodiment of the ultrasound system 1, comprising controller 20 and ultrasound array transducer 5, is shown. Although the controller 20 and the ultrasound array transducer 5 are shown as separate modules, it should be understood that the components of each may be embodied in one module. The controller 20 may control the ultrasound array transducer 5 over wired or wireless communications, as known to one skilled in the art. The controller 20 may be a dedicated hand-held unit, a personal computing device, or a component of a larger control system.

As described above, the ultrasound array transducer 5 may vary in configuration and size, and can be designed in various ways as known in the art. The plurality of transducer elements 10 each have piezoelectric elements that vibrate to produce acoustic energy (ultrasound energy) when an electrical current is supplied to the piezoelectric element. The microcontroller 60 may perform steps stored in ROM 63 to initialize the ultrasound system 1. The microcontroller 60 is configured to control the supply of power to the transducer elements 10 (shown as a single transducer element 10 for simplicity) so that the transducer elements 10 can be actuated to deliver particular intensity levels of acoustic signal at specific times. The selections of the various intensity levels and various times allows the ultrasound system 1 to provide focused acoustic energy 25 at the required intensity levels, frequencies, duty cycles, focal zone sizes, focal zone locations, focal zone scan rates, and sweep rates for optimal tissue growth. It is understood that the microcontroller 60 may include related hardware and software, and may be any processor capable of performing the steps of the different methods of the present invention.

To initialize the ultrasound system 1, the user may be prompted for treatment locations and parameters on the display 85. The display 85 may display treatment settings and other information. The user may input his/her selections into the input device 90. The input device 90 may be a touch screen, a keyboard, a mouse, a dial, or any other similar device. Conversely, the microcontroller 60 may initialize the ultrasound system 1 based on preprogrammed parameters stored in ROM 63. During initialization, the microcontroller 60 may set a timer 64 to monitor the duration of the treatment and other assorted durations, such as rest periods. The microcontroller 60 may also determine the specific energy and timing signals for each transducer element 10 for the treatment duration. This information may then be stored in the FIFO memory 65 as an output profile.

In order to actuate the transducer elements 10 to emit the focused acoustic energy 25 at the required intensity levels, frequencies, duty cycles, phase intervals, focal zone scan rates, sweep rates, and treatment durations; the microcontroller 60 may read the output profile from the FIFO memory 65 and at time periods generated by the oscillator 80, control the signals to the drivers 67. To accomplish this, the microcontroller 60 may control the power converters 70 to convert the power level from the power supply 75 to a power level required by the drivers 67 to actuate the transducer elements 10 to emit the focused acoustic energy 25 at the necessary energy level. At a corresponding time, the controller 60 may control the pulse generators 66 to supply the converted power signals to the drivers 67 to actuate the plurality of transducer elements 10 at the required time to generate the focused acoustic energy 25. The power converters 70, pulse generators 66, and drivers 67 are depicted in FIG. 8 as single components, but it is understood that each may be a plurality of components matching the plurality of transducer elements 10 (or a subset). It should be appreciated that various components can be incorporated to accomplish the foregoing, as known by one skilled in the art.

Figure 9:
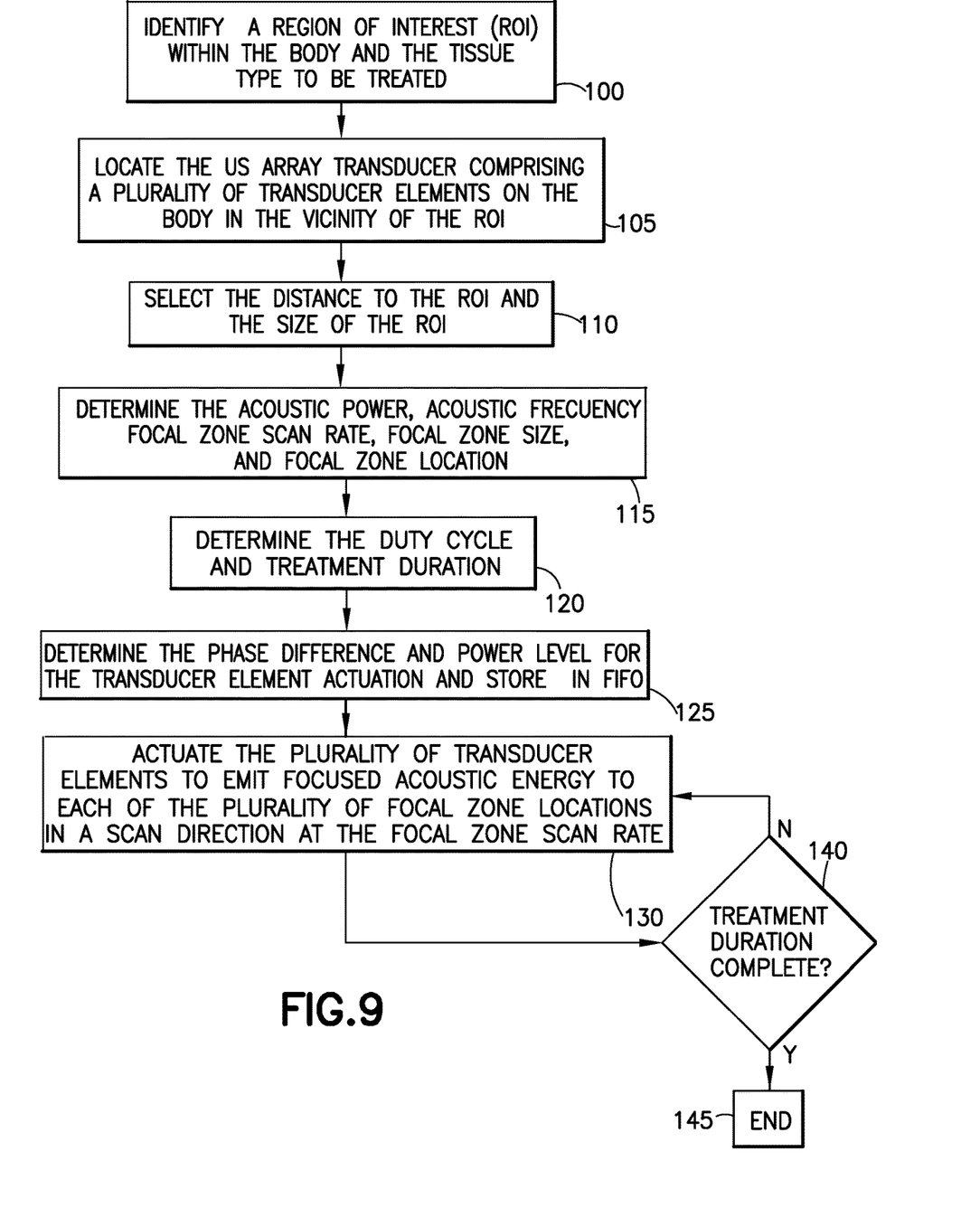
FIG. 9 shows a flow diagram that illustrates an embodiment of a method for stimulating cell activity within tissue.

Referring to FIG. 9, an example method of the present invention will be described. In this example, the ROI may be identified and the type of tissue to be treated may be selected, step 100, by a medical professional, a therapist, or a user of the therapy system. The ROI may be determined using various imaging systems, including ultrasound, MRI, CT scan, and x-rays. In various embodiments the type of tissue and/or the ROI may be preprogrammed into the ultrasound system 1.

The ultrasound array transducer 5 is then placed on the body 15 in the vicinity of the ROI, step 105. In some embodiments, the body 15 may be a container holding the tissue to be treated. The ultrasound array transducer 5 may be acoustically coupled to the skin of a body 15 by applying gel to the surface of the body 15 or the ultrasound array transducer 5. Alternatively, the ultrasound array transducer 5 may be acoustically coupled to the body using water (or a water bath), as known to one skilled in the art. In certain embodiments, the ultrasound array transducer 5 is placed on the tissue to be treated.

Next, the distance to the ROI is selected, step 110. This distance may be pre-programmed in various embodiments. Next the acoustic power, acoustic frequency, focal zone scan rate, and focal zone locations are determined, step 115, as described above. Next the duty cycle and the treatment duration are determined, step 120. This may be a function of the selected type of tissue to be treated, as described above. Next the timing and power level parameters for the transducer element 10 actuation are determined and this data is stored in the FIFO memory 65, step 125. In certain embodiments, the duty cycle, treatment duration, power levels and timing may be pre-programmed into the ultrasound system 1, causing these steps to be unnecessary. Next the controller 20 actuates the plurality of transducer elements 10 to emit focused acoustic energy 25 to the plurality of focal zone locations at the focal zone scan rate, step 130. Next, for each sweep cycle the controller 20 determines if the treatment duration is completed, step 140. If the treatment duration is not completed, the step of actuating the plurality of transducer elements 10 to emit focused acoustic energy 25 to the plurality of focal zone locations at the focal zone scan rate will be initiated. When the treatment duration is completed, the controller 20 will stop emitting the focused acoustic energy 25, step 145. It should be appreciated that the above steps can be performed in many variations and with additional steps incorporated to accomplish the foregoing, as known by one skilled in the art.

While the above is a complete description of selected embodiments of the present invention, it is possible to practice the invention using various alternatives, modifications, combinations and equivalents. For example, ultrasound transducers with a single transducer element may work in concert with other ultrasound transducers with a single transducer element strategically located on the body to accomplish the method of the present invention. In addition, an annular array format may be used instead of two-dimensional format. In general, in the following claims, the terms used should be construed to include all possible embodiments along with the full scope of equivalents to which such claims are entitled. Accordingly, the claims are not limited by the disclosure.

I claim:

1. A method of stimulating cell activity by mechanical loading of a tissue at a region of interest (ROI), the method comprising:
   locating in a vicinity of the ROI an ultrasound array transducer, the ultrasound array transducer comprising a plurality of transducer elements;
   actuating the plurality of transducer elements to emit focused acoustic energy at a loading rate to each focal zone of a plurality of focal zone locations in a scan direction at a focal zone scan rate; and
   repeating the actuating for a plurality of sweep cycles at a predetermined sweep rate,
   wherein the emitted focused acoustic energy induces pressure gradients that press on sides of cells in each focal zone of the plurality of focal zone locations, and
   wherein the predetermined sweep rate is twice the loading rate.

2. The method of claim 1, wherein the scan direction is opposite for alternate sweep cycles.

3. The method of claim 1, wherein actuating the plurality of transducer elements to emit focused acoustic energy to the plurality of focal zone locations is performed in two spatial dimensions.

4. The method of claim 1, wherein actuating the plurality of transducer elements to emit focused acoustic energy to the plurality of focal zone locations is performed in three spatial dimensions.

5. The method of claim 1, wherein the focused acoustic energy has an intensity in the range of 5 mW/cm$^2$ to 180 mW/cm$^2$ at the ROI.

6. The method of claim 1, wherein the loading rate is greater than 0.1 Hz.

7. The method of claim 1, wherein the focal zone locations are uniformly spaced throughout the ROI.

8. The method of claim 1, wherein performing the plurality of sweep cycles at the predetermined sweep rate is performed for a treatment duration, the treatment duration having a time range of five minutes to sixty minutes.

9. The method of claim 8, wherein the treatment duration further comprises a rest period.

10. A system for stimulating cell activity within a body at a region of interest (ROI), the system comprising:
    an ultrasound array transducer, the ultrasound array transducer comprising a plurality of transducer elements; and
    a controller programmed to:
    actuate the plurality of transducer elements to emit focused acoustic energy at a loading rate to each focal zone of a plurality of focal zone locations in a scan direction at a focal zone scan rate; and repeat the actuating for a plurality of sweep cycles at a predetermined sweep rate,
wherein the emitted focused acoustic energy induces pressure gradients that press on sides of cells in each focal zone of the plurality of focal zone locations, and
wherein the predetermined sweep rate is twice the loading rate.

11. The system of claim 10, wherein the ultrasound array transducer is in a linear format.

12. The system of claim 10, wherein the ultrasound array transducer is in a two-dimensional matrix format.

13. The system of claim 10, wherein the focused acoustic energy has an intensity in the range of 5 mW/cm$^2$ to 180 mW/cm$^2$ at the ROI.

14. The system of claim 10, wherein the loading rate is greater than 0.1 Hz.

15. The system of claim 10, wherein the focal zone locations are uniformly spaced throughout the ROI.

16. The system of claim 10, wherein the controller is further configured to actuate, for a plurality of sweep cycles at a predetermined sweep rate, and wherein performing the plurality of sweep cycles at the predetermined sweep rate is performed for a treatment duration, the treatment duration having a time range of five minutes to sixty minutes.

17. A controller for stimulating cell activity within a body at a region of interest (ROI), the controller programmed to:
actuate a plurality of transducer elements to emit focused acoustic energy at a loading rate to each focal zone of a plurality of focal zone locations in a scan direction at a focal zone scan rate; and
repeat the actuating for a plurality of sweep cycles at a predetermined sweep rate,
wherein the predetermined sweep rate is twice the loading rate, and
wherein the emitted focused acoustic energy induces pressure gradients that press on sides of cells in each focal zone of the plurality of focal zone locations.

18. The controller of claim 17, wherein the loading rate is greater than 0.1 Hz.

19. The system of claim 18, wherein the scan direction is opposite for alternate sweep cycles.

* * * * *